(12) United States Patent
Clasen (10) Patent No.: US 7,667,834 B2
(45) Date of Patent: Feb. 23, 2010

(54) METHOD AND CONFIGURATION FOR DETECTING MATERIAL DEFECTS IN WORKPIECES

(75) Inventor: Ralf Clasen, München (DE)

(73) Assignee: Automation W + R GmbH, Munich (DE)

( * ) Notice: Subject to any disclaimer, the term of this patent is extended or adjusted under 35 U.S.C. 154(b) by 0 days.

(21) Appl. No.: 12/139,909

(22) Filed: Jun. 16, 2008

(65) Prior Publication Data

US 2008/0297780 A1    Dec. 4, 2008

Related U.S. Application Data

(63) Continuation of application No. PCT/EP2006/012074, filed on Dec. 14, 2006.

(30) Foreign Application Priority Data

Dec. 16, 2005   (DE) .................. 10 2005 060 735
Mar. 24, 2006   (DE) .................. 10 2006 013 655

(51) Int. Cl.
*G01N 21/00* (2006.01)

(52) U.S. Cl. .................. 356/237.1; 356/237.2

(58) Field of Classification Search ... 356/237.1–237.5, 356/239.1–239.8
See application file for complete search history.

(56) References Cited

U.S. PATENT DOCUMENTS 4,976,540 A * 12/1990 Kitamura et al. .............. 356/38
5,115,136 A    5/1992 Tomasch
5,249,029 A *  9/1993 Sommer et al. ............. 356/336
5,554,318 A    9/1996 Neumann et al.
6,392,754 B1 * 5/2002 Pingel et al. ................ 356/603
6,626,047 B1   9/2003 Vetterlein
6,697,514 B1   2/2004 Kobayashi et al.
7,241,399 B2   7/2007 Haubold et al.

FOREIGN PATENT DOCUMENTS

| DE | 29902218 U1 | 6/1999 |
| EP | 0282627 A2 | 9/1988 |
| EP | 0666474 A1 | 8/1995 |
| GB | 2222879 A | 3/1990 |
| JP | 2000258398 A | 9/2000 |
| WO | 0220696 A1 | 3/2002 |

OTHER PUBLICATIONS

International Search Report, dated Mar. 15, 2007.

* cited by examiner

*Primary Examiner*—Hoa Q Pham
(74) *Attorney, Agent, or Firm*—Laurence A. Greenberg; Werner H. Stemer; Ralph E. Locher (57) ABSTRACT

A method and a configuration for automatically or visually detecting material defects, in particular cracks, in a workpiece, includes applying a test agent to the workpiece. The test agent contains color pigments which can be excited by using shortwave light. The workpiece is then irradiated with shortwave light from a light source, light emitted by the workpiece is detected by an observer's eye or by a detector, and the signals from the detector are evaluated by an electronic evaluation device in order to determine the material defects. The light source is associated with a first optical interference filter which selects the light emitted by the light source, as a bandpass filter, before the light impinges on the workpiece.

30 Claims, 4 Drawing Sheets

METHOD AND CONFIGURATION FOR DETECTING MATERIAL DEFECTS IN WORKPIECES

CROSS-REFERENCE TO RELATED APPLICATIONS

This is a continuation, under 35 U.S.C. § 120, of International Application No. PCT/EP2006/012074, filed Dec. 14, 2006, which designated the United States; this application also claims the priority, under 35 U.S.C. § 119, of German Patent Application Nos. DE 10 2005 060 735.7, filed Dec. 16, 2005, and DE 10 2006 013 655.1, filed Mar. 24, 2006; the prior applications are herewith incorporated by reference in their entirety.

BACKGROUND OF THE INVENTION

Field of the Invention

The invention relates to a method for detecting material defects, in particular cracks, in a workpiece, which includes exposing the workpiece to a test agent containing color pigments that can be excited by shortwave light. The workpiece is subsequently irradiated with shortwave light from a light source, the light emitted by the workpiece is detected by a detector and the signals of the detector are evaluated by an electronic evaluation device in order to determine the material defects, or the light emitted by the workpiece is detected by the eye of a human observer. The light source is assigned a first optical interference filter which selects the light emitted by the light source in the manner of a bandpass filter, before it impinges on the workpiece.

The invention also relates to a configuration for detecting material defects, in particular cracks, in a workpiece which is exposed to a test agent containing color pigments that can be excited by light, in order to carry out the method according to the invention. The configuration includes a light source which irradiates the workpiece with light, a detector that detects the light emitted by the workpiece and an electronic evaluation device which evaluates signals of the detector in order to determine the material defects. The light source is associated with a first optical interference filter which selects the light emitted by the light source in the manner of a bandpass filter, before it impinges on the workpiece.

In the field of testing materials, methods in which the workpieces are subjected to a colorant particle-containing solution or to a powder and subsequently irradiated with shortwave light by an illuminating device, in particular in the form of a UV lamp, are used to optically determine damage and cracks in workpieces.

Irradiation using shortwave light excites the color pigments to emit fluorescent or phosphorescent light which is detected either visually by the eye of an observer or using cameras which are coupled to an electronic evaluation device that determines, from the recorded light intensities, material defects, in particular cracks, on which the color particles are preferably deposited.

In order to enhance the contrast in magnetizable test pieces, provision may be made in such a case for the color pigments to be bound to magnetizable particles, such as to magnetic powder or iron filings, in order to obtain increased deposits of color pigments in the region of cracks resulting from the scattered fields which are formed due to an external magnetic field being applied to the workpieces.

A fundamental problem when visually testing workpieces according to the above-described methods is that not only does the mandatory use of shortwave light in the UV range generally result in the human eye being greatly stressed, but that, in the case of direct contact with the shortwave radiation, the skin and other organs may also be damaged, with the risk thereof increasing particularly strongly if the intensity of the exciting UV light is increased in order to obtain a sufficiently high contrast, even for small cracks, which enables visual detection thereof by the human eye of an observer in the first place.

Such a high contrast between cracks and undamaged surface portions of a workpiece is, however, inevitably necessary for a fault-free visual inspection, since it is only in that manner that fatigue-free working even over a relatively long period of time is made possible in the first place.

For that reason, flash lamps, for example, which are often used in automatic workpiece inspection, are generally not suitable for the visual inspection of the workpieces, since the strongly fluctuating light intensities of the flash lamps, in conjunction with the inertia of the human eye, lead to a blinding effect which rules out the possibility of detecting defects in a workpiece.

German Utility Model DE 299 022 18 U1, corresponding to U.S. Pat. No. 6,626,047, discloses a method of the above-described type in which light-emitting diodes (LEDs) which are known for illuminating the test pieces and emit light with a wavelength in a range between 200 nm and 970 nm, are used. Although use of LEDs entails a significant increase in the service life of the illuminating device relative to the otherwise usually employed UV flash lamps, the UV light produced by the LEDs has a comparatively large spectral range and low intensity so that, compared to UV flash lamps, a low contrast results, which means cracks in non-homogeneous workpiece surfaces can only be detected with difficulty. That drastically increases the error rate in an automatic crack inspection of moving workpieces.

SUMMARY OF THE INVENTION

It is accordingly an object of the invention to provide a method and a configuration which can be used to detect material defects in inhomogeneous workpiece surfaces, which overcome the hereinafore-mentioned disadvantages of the heretofore-known methods and configurations of this general type and which do so with a high degree of reliability.

With the foregoing and other objects in view there is provided, in accordance with the invention, a method for detecting material defects, such as cracks, in a workpiece. The method comprises exposing the workpiece to a test agent containing color pigments to be excited by shortwave light, subsequently irradiating the workpiece with shortwave light from a light source having a plurality of LEDs disposed in a matrix, assigning to the light source a first optical interference filter selecting the light emitted by the light source as a bandpass filter, before the light impinges on the workpiece, detecting light emitted by the workpiece with a detector, and evaluating signals of the detector with an electronic evaluation device for determining the material defects or detecting the light emitted by the workpiece with an eye of a human observer.

With the objects of the invention in view there is also provided a configuration for detecting material defects, such as cracks, in a workpiece exposed to a test agent containing color pigments to be excited by light. The configuration comprises a light source irradiating the workpiece with light, the light source having a plurality of LEDs disposed in a matrix, a first optical interference filter associated with the light source for selecting light emitted by the light source as a bandpass filter, before the light impinges on the workpiece, a detector detecting light emitted by the workpiece, and an electronic evaluation device evaluating signals of the detector for determining the material defects and carrying out the method according to the invention.

With the objects of the invention in view there is additionally provided a configuration for detecting material defects, such as cracks, in a workpiece exposed to a test agent containing color pigments to be excited by light. The configuration comprises a light source irradiating the workpiece with shortwave light exciting the color pigments, the light source having a plurality of LEDs disposed in a matrix, a first optical interference filter associated with the light source for selecting light emitted by the light source as a bandpass filter, before the light impinges on the workpiece, the workpiece emitting light to be detected by an eye of a human observer, for carrying out the method according to the invention, and a second optical filter to be associated with the eye of the observer for selecting the light emitted by the workpiece as a further bandpass filter, before the light impinges on the eye of the observer.

According to the invention, in a method for automatically detecting material defects, in particular cracks in or on workpieces, which were previously sprayed with, or immersed in, a test agent, in particular a test solution including color pigments, the workpiece is subsequently irradiating with shortwave light, in particular with light from a UV or a blue light source, the light emitted by the workpiece is detected with a detector and the signals of the detector are evaluated with an electronic evaluation device in order to determine the material defects. The color pigments in this case are preferably fluorescing or phosphorescing substances which are sold in the desired wavelength ranges, for example under the trademark "Lumogen Yellow" from BASF AG in Ludwigshafen, Germany.

In this case, the workpieces can also be subjected, in particular, to a magnetic field, wherein the solution in this case contains colorant pigment-bound magnetic or magnetizable particles, such as iron particles, which are deposited, after the magnetic field is applied, on the edges of cracks with increased concentration. Irradiating with shortwave light causes the color particles to emit fluorescent light, through the use of which the cracks are made visible to an observer in the form of crack worms.

In accordance with another feature of the invention, the color pigments can preferably be excited in the preferred embodiment of the invention by light in a wavelength range between 300 nm and 480 nm, with the light source preferably producing the light in a wavelength range between 460 nm and 490 nm.

In accordance with a further feature of the invention, in order to increase the contrast, the light source is associated with a first optical interference filter which selects the light emitted by the light source, preferably blue light, in the manner of a bandpass filter, before it impinges on the workpiece.

In accordance with an added feature of the invention, the first optical interference filter in this case has a transmission range, i.e. a range in which the light of a prespecified wavelength can pass through the filter in a virtually unimpeded fashion, which is between 380 nm and 480 nm. The transmission or the transmissivity of the optical interference filter in the transmission region in this case is preferably above 90%, particularly preferably even above 98%.

In accordance with an additional feature of the invention, the detector is associated with a second optical interference filter which selects, in a wavelength-specific fashion, the fluorescent or phosphorescent light emitted by the workpiece in the manner of a bandpass filter, before it impinges on the detector.

Although the above-mentioned wavelength ranges of the first filter and the absorption range of the color pigments can also be chosen to be different or can be shifted, a second interference filter having a transmission range for the irradiated light between 500 nm and 580 nm is chosen, in particular, in combination with the wavelength ranges for the excitability of the color pigments (300 nm-480 nm) and the wavelength range for the light source (460 nm-490 nm) and the transmission range of the first optical interference filter (380 nm-480 nm).

The applicant was surprisingly able to observe, in combination with color pigments emitting fluorescent light or phosphorescent light in the range between 500 nm and 600 nm after their excitation, a particularly high contrast, which makes automatic detection of the smallest cracks or other damage on surfaces of continuously moving workpieces in practice possible in the first place.

It has furthermore surprisingly been found in this case that due to the additional restriction of the excitation spectrum by way of the first optical interference filter which has a very steep-sided absorption range, in particular between 380 nm and 480 nm compared to a similar apparatus in which such a filter is not used, an additional contrast increase can be observed, which can be increased even further by using a narrow-band LED that emits bluish light in the range between 460 nm and 490 nm as a light source.

The first and preferably also the second interference filter include a plurality of thin layers of a dielectric, transparent material such as mica or suitable polymers which are vapor-deposited at high vacuum onto a suitable substrate such as, in particular, a glass carrier. The reflections of an incoming light beam at the interfaces of two adjoining layers and the subsequent superposition of the reflected waves result in interference phenomena, due to which, as a function of the thickness of the thin layers, light of a specific wavelength range is extinguished by way of destructive superposition. However, light with a wavelength in the transmission range of the filter passes through the latter in a virtually unimpeded fashion.

According to a further concept based on the invention, the detection rate of cracks and surface defects in moving workpieces, such as workpiece blanks in a foundry, can be increased further by using a large number of semiconductor LEDs as the light source in order to illuminate the workpiece. The LEDs are disposed in one plane in the manner of a matrix or an array and the bluish light of which, with a wavelength in the range between 460 nm and 490 nm, is emitted substantially parallel in the direction of the workpiece. Although in this case, each LED can be assigned its own first optical interference filter, preferably a common interference filter for the entire diode matrix of 4×4 LEDs, for example, is used.

In order to increase the light intensity further, it is additionally possible for a plurality of light sources in the form of diode arrays to be provided as well, which irradiate the workpiece while it moves continuously from a plurality of sides and, if appropriate, in a superposing fashion.

Although a UV flash lamp, that is likewise known, for example, from the prior art, with a suitable spectrum can be used as the light source, in the preferred embodiment of the invention the light source in the form of the LEDs is preferably operated continuously, which provides the additional advantage that, during the recording process of moving workpieces, the workpiece movement does not need to be synchronized with the light source.

As the applicant was able to observe in this case, in particular when using LEDs which are disposed in the manner of a matrix, such a high intensity is obtained, despite the radiation intensity which is significantly reduced with respect to UV flash lamps, due to the superposition of the light intensities of the individual LEDs in a matrix and due to the light waves being irradiated substantially parallel at a large solid angle range. Therefore, even with continuously moving workpieces in combination with a continuously operating light source, the color pigments are excited sufficiently strongly by the light source, through the use of which the intensity of the fluorescent or phosphorescent light that is shifted towards a greater wavelength leads to signals in the downstream detector despite the interconnected first and/or second interference filter(s). The signals, with the use of known image processing methods, make it possible to reliably detect small cracks which could, for example, be 20 µm wide with a speed of the workpiece of, for example, 1 m/s.

In accordance with yet another feature of the invention, the detector is in the form of a CCD-line camera with at least one CCD line in which, with continuous movement of the workpiece, the reading of the light-sensitive cells of the CCD line is preferably effected with a speed which is proportional to the speed of the workpiece.

In accordance with yet a further feature of the invention, in the preferred embodiment, the CCD-line camera, when viewed in the movement direction of the workpiece, has at least two, but preferably 64 or more, adjoining CCD lines, in which two neighboring light-sensitive cells, referred to below as corresponding light-sensitive cells, are disposed next to each other along an axis which is preferably in the form of a straight line extending parallel to the movement direction of the workpiece when the workpiece is moved in a straight line.

In accordance with yet an added feature of the invention, in order to further increase the detection rate in this refinement of the invention, provision may be made for the signal values which are read from the mutually corresponding light-sensitive cells of the CCD lines to be added, which can be done, for example, in digital form by correspondingly storing and adding the signal values in the electronic evaluation device with the aid of a microprocessor. However, it is likewise feasible for the signals of two or more corresponding light-sensitive cells to be added electronically by way of using known electronic components if these are read at a speed which corresponds to the workpiece speed. This results in the advantage that the intensity of the fluorescent light emitted by a crack is registered one after the other by each of the corresponding cells as the workpiece moves past and produces there a signal value which corresponds to the incoming intensity of the emitted light. Although the magnitude of the signal value of a single cell in the case of small cracks sometimes does not suffice for identifying a crack beyond doubt, the signal value, which is integrated up, increases by a factor which corresponds, at a constant light intensity, substantially to the number of the corresponding light-sensitive cells due to the addition, according to the invention, of the signal values of a plurality or all of the corresponding light-sensitive cells which are disposed on an axis that extends parallel to the movement direction of the workpiece.

This provides the option of obtaining a signal height necessary for the reliable detection of cracks due to a corresponding increase in the number of the CCD lines even in the case of very weak light signals or in the case of high workpiece speeds and a constant illumination with a comparatively low intensity.

In accordance with yet an additional feature of the invention, the light emitted by the workpiece is detected by the eye of a human observer carrying out a visual inspection of the workpiece, with the appropriate use of the above-described teaching in a method for visually detecting material defects such as cracks in or on workpieces which were previously sprayed with, or immersed in, a test agent, in particular a test solution, which includes color pigments and in which the workpiece is subsequently irradiated with shortwave light, in particular with light from a UV or a blue light source. The color pigments in this case are preferably fluorescing or phosphorescing substances which are sold in the desired wavelength ranges, for example under the trademark "Lumogen Yellow" from BASF AG in Ludwigshafen, Germany.

In accordance with again another feature of the invention, in this case, the workpieces can also be subjected, in particular, to a magnetic field, wherein the solution in this case contains colorant pigment-bound magnetic or magnetizable particles, such as iron particles, which are deposited, after the magnetic field is applied, on the edges of cracks with increased concentration. Irradiating with shortwave light causes the color particles to emit fluorescent light, through the use of which the cracks are made visible to the observer in the form of crack worms.

In accordance with again a further feature of the invention, the color pigments can preferably be excited in the preferred embodiment of the invention by light in a wavelength range between 300 nm and 480 nm, with the light source preferably producing the light in a wavelength range between 460 nm and 490 nm.

In the same manner as in the above-described method for automatic crack detection, in the case of visual detection of material defects in workpieces, the light source is also associated, in order to increase the contrast, with a first optical filter, in particular an interference filter, which selects the light emitted by the light source, preferably blue light, in the manner of a bandpass filter, before it impinges on the workpiece. The eye of the observer carrying out the visual inspection is associated with a second optical filter, in particular likewise an interference filter, which selects, in a wavelength-specific fashion, the light emitted by the workpiece in the manner of a further bandpass filter, before it impinges on the eye. The second optical filter can, however, also be an optically active film, for example a polyethylene or polyurethane film which likewise filters the light, in a wavelength-specific fashion, in the manner of a bandpass filter.

In accordance with again an added feature of the invention, the first optical interference filter in this case has a transmission range, i.e. a range in which the light of a prespecified wavelength can pass through the filter in a virtually unimpeded fashion, which is between 380 nm and 480 nm. The transmission or the transmissivity of the optical interference filter in the transmission region in this case is preferably above 90%, particularly preferably even above 98%.

Although the above-mentioned wavelength ranges of the first filter and the absorption range of the color pigments can also be chosen to be different or can be shifted, a second optical filter having a transmission range for the irradiated light between 500 nm and 580 nm in the case of an optical interference filter is chosen, in particular, in combination with the wavelength ranges for the excitability of the color pigments (300 nm-480 nm) and the wavelength range for the light source (460 nm-490 nm) and the transmission range of the first optical filter (380 nm-480 nm).

In combination with color pigments emitting fluorescent light or phosphorescent light in the range between 500 nm and 600 nm after their excitation, the applicant was surprisingly able to observe a particularly high contrast which makes visual detection that is easy on the eye of even the smallest cracks or other damage on the surfaces of workpieces in practice possible in the first place.

It has furthermore surprisingly been found in this case that due to the additional restriction of the excitation spectrum by way of the first optical filter which, when it is in the form of an interference filter, has a very steep-sided transmission range between, in particular, 380 nm and 480 nm compared to a comparative apparatus in which such a filter is not used, an additional contrast increase can be observed, which can be increased even further by using a narrow-band LED as the light source which emits bluish light in the range between 460 nm and 490 nm.

Even in the case of the visual crack detection by way of the eye of an observer, the first and preferably also the second interference filter preferably include a plurality of thin layers of a dielectric transparent material such as mica or suitable polymers which are vapor-deposited at high vacuum onto a suitable substrate such as, in particular, a glass carrier. The reflections of an incoming light beam at the interfaces of two adjoining layers and the subsequent superposition of the reflected waves result in interference phenomena due to which, as a function of the thickness of the thin layers, light of a specific wavelength range is extinguished by way of destructive superposition, whereas light with a wavelength in the transmission range of the filter passes through the latter in a virtually unimpeded fashion.

The applicant has further found that surprisingly a good optical contrast can still be obtained in the case of the visual observation of cracks in the above-described manner if, according to another embodiment of the invention, a substantially less expensive plastic film, in particular an illuminator film, is used rather than the second optical interference filter. The plastic film has a substantially bell-shaped transmission range between 460 nm and 620 nm with a transmission maximum in the range between 500 nm and 550 nm, in particular 510 and 530 nm, for the light emitted by the workpiece. The use of such a film, which may be made, for example, of polypropylene or else another polymer, provides the advantage firstly that it can be bought inexpensively as bulk goods in relatively large amounts and, secondly, that it can be matched very easily by appropriately cutting it to the shape of optical auxiliary devices such as, in particular, spectacles or eyeglasses etc., and/or can be applied to the latter for example by way of adhesive bonds. The above-mentioned optically active films can likewise be used to produce, in a very cost-effective manner, cover-glasses which can also be worn by spectacle or eyeglass wearers over their actual visual aid in the manner of ski goggles in order to carry out a visual inspection according to the method of the invention.

According to another concept based on the invention, it is possible to further increase the detection rate of cracks and surface defects in resting or moving workpieces, such as workpiece blanks in a foundry, by using as the light source a large number of semiconductor LEDs for illuminating the workpiece. The semiconductor LEDs are disposed in one plane in the manner of a matrix or an array and the bluish light thereof with a wavelength in the range between 460 nm and 490 nm is emitted substantially parallel in the direction of the workpiece. Although in this case each LED can be assigned its own first optical interference filter, a common interference filter for the entire diode matrix of, for example, 4×4 LEDs, is preferably used.

In order to increase the light intensity further, it is additionally possible for a plurality of light sources in the form of diode arrays to be provided as well, which irradiate the workpiece from a plurality of sides and, if appropriate, in a superposing fashion. The workpiece is irradiated in this case by way of a continuous operation of the LEDs, which results in the additional advantage of a particularly still image for the human eye.

As the applicant was able to observe in this case, in particular when using LEDs which are disposed in the manner of a matrix, such a high intensity is obtained, despite the radiation intensity which is significantly reduced with respect to UV flash lamps and due to the superposition of the light intensities of the individual LEDs in a matrix and the light waves being irradiated substantially parallel at a large solid angle range that, even with continuously moving workpieces in combination with a continuously operating light source, the color pigments are excited sufficiently strongly by the light source. The intensity thereof suffices for the observer to perceive the damaged regions, despite the interconnected first and second interference filters, as crack worms which radiate clearly more brightly.

In accordance with again an additional feature of the invention, in this case, the light source, the workpiece and the second optical filter are disposed spatially in relation to each other in such a manner that light which is emitted exclusively by the workpiece directly falls through the second optical filter onto the eye of the observer.

In accordance with still another feature of the invention, a protection device, for example in the form of a wall which is not transparent for the light, is disposed between the eye of the observer and the workpiece. The protection device prevents light, which is scattered by the workpiece or surrounding objects laterally past the second optical filter in the direction of the eye, from falling directly onto the eye of the observer. As the applicant was able to observe, this can once more increase the contrast, since scattered radiation from surrounding objects does not reach the eye and result in disturbing light reflexes there.

In accordance with still a further feature of the invention, the observer observes the workpiece through a viewing pane which includes the second optical filter, is disposed between the workpiece and the observer and can be incorporated, for example, in the protection device.

In accordance with a concomitant feature of the invention, in the same way, there is the option of configuring the second interference filter as a spectacle or eyeglass lens which is incorporated in appropriate protective goggles. The spectacles or eyeglasses can be provided with a known side protection which is associated with at least one of the two eyes of the observer and prevents lateral infiltration of scattered light.

The use of such spectacles or eyeglasses, where preferably both lenses are configured as second optical filters, in particular interference filters or else optical film or films, enables free, unimpeded working of the observer who can rotate the workpiece freely using his or her hands into the desired position for the purposes of a visual inspection in the region of the incoming shortwave light of the light source or light sources. It is not even necessary in this case, when using an above-described matrix including high-power LEDs emitting bluish light, to wear specific protective clothing such as UV-resistant gloves or other UV-resistant protective clothing, since the light intensity is lower as compared to known UV vapor lamps by orders of magnitude and the wavelength of the emitted light is in the bluish range rather than the UV range.

Other features which are considered as characteristic for the invention are set forth in the appended claims.

Although the invention is illustrated and described herein as embodied in a method and a configuration for detecting material defects in workpieces, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
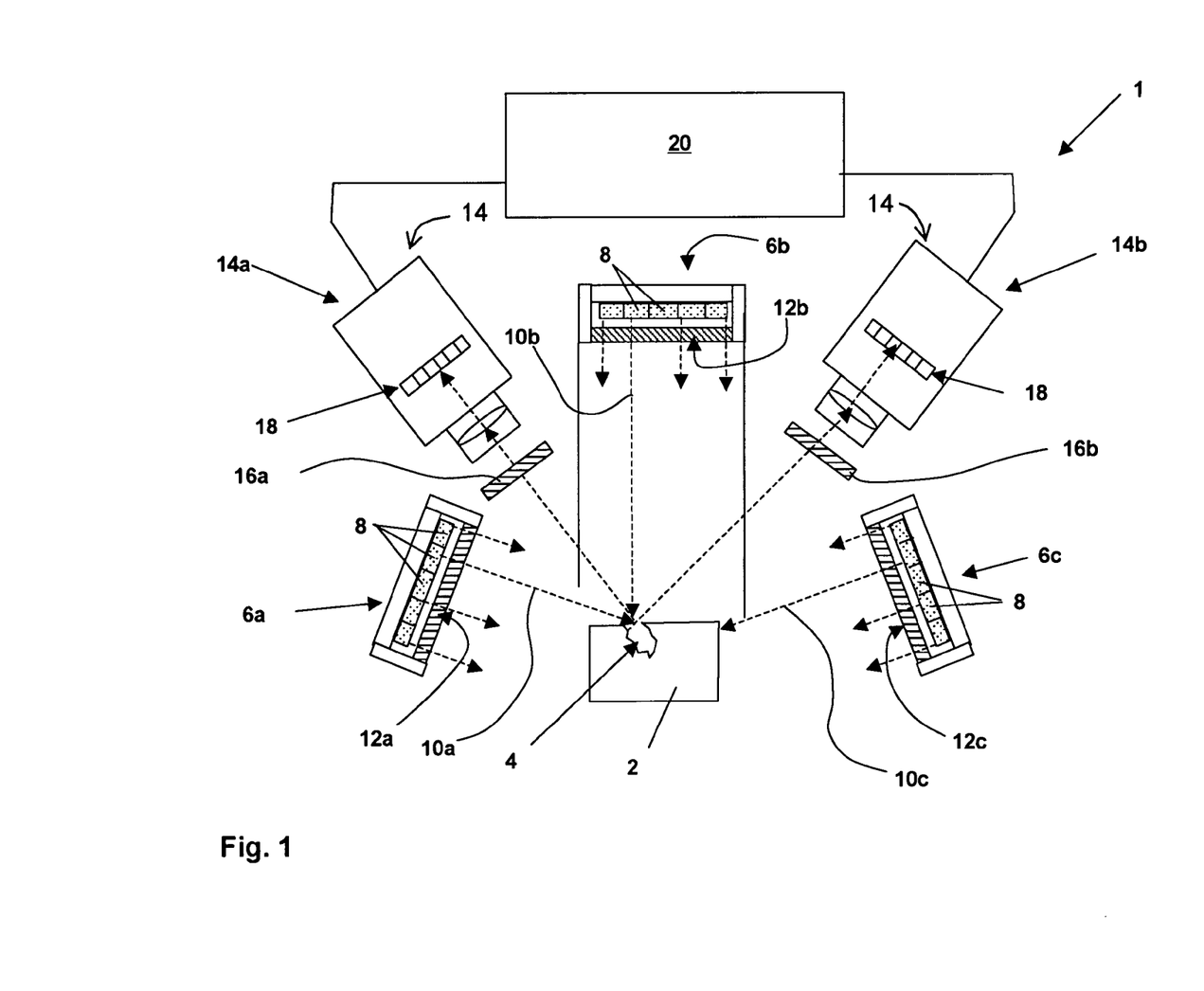
FIG. 1 is a diagrammatic, top-plan view of a configuration according to the invention with three light sources and two detectors overall, which are disposed over an angle area of about 160° around a workpiece that moves out of the plane of the drawing and into the latter.

Referring now to the figures of the drawings in detail and first, particularly, to FIG. 1 thereof, there is seen a configuration 1 according to the invention for automatically detecting material defects in a workpiece 2, which defects occur, in particular, in the form of cracks 4 that are illustrated in a clearly larger scale in the drawings for illustrative reasons.

Figure 2:
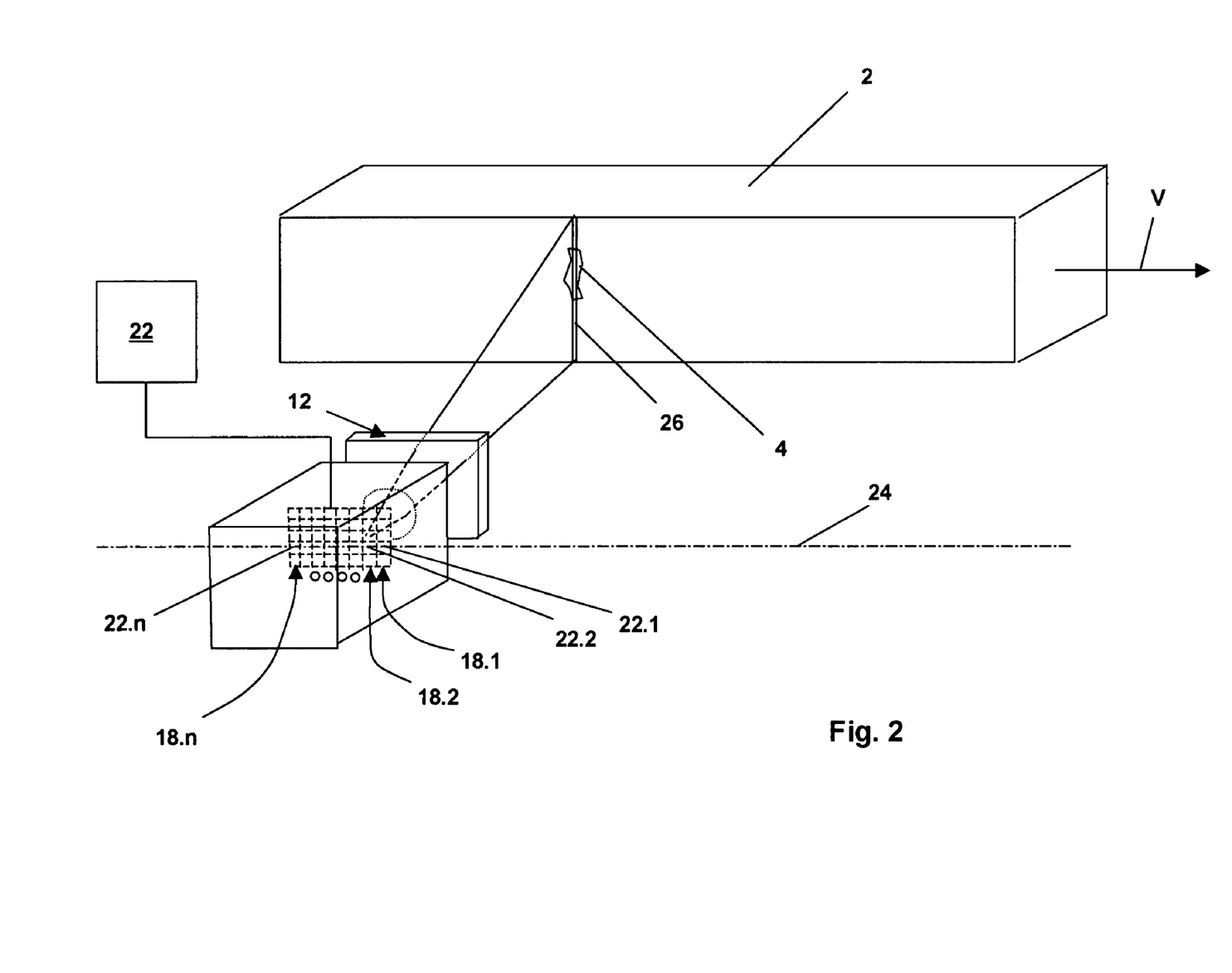
FIG. 2 is a perspective view of a detector according to the invention in the form of a CCD-line camera with a plurality of adjoining CCD lines, during the detection of a workpiece which moves past the detector with a continuous speed.

The workpiece or workpieces 2 are transported in this case through a non-illustrated transport device, such as a gripper or a conveyor belt, with a constant speed which is indicated by an arrow V in the workpiece 2 in FIG. 2. The movement direction of the workpiece 2 in FIG. 1 extends into the plane of the drawing and out of that plane.

The workpiece 2 was previously exposed to a solution in a known manner, for example immersed therein or sprayed with it, with the solution including fluorescing or phosphorescing color pigments which can be excited by shortwave light, for example blue light or UV light, and emitting the irradiated light again as longer-wave fluorescent or phosphorescent light.

The color particles in this case are preferably deposited in the cracks 4 of the workpieces 2 and become visible as crack worms when irradiated by using shortwave light in a known manner.

In the configuration 1 according to the invention which is shown in FIG. 1, the shortwave light is preferably produced by three light sources 6a, 6b and 6c each of which includes a large number of LEDs 8 that are disposed in a planar fashion in one plane, preferably in the manner of a matrix, and emit their light in the form of light beams 10a, 10b and 10c in the direction of the workpiece 2.

One respective first optical interference filter 12a, 12b and 12c is disposed between each of the light sources 6a, 6b and 6c and the workpiece 2 in a manner according to the invention. The interference filter selects the light 10a, 10b and 10c emitted by the light sources 6a, 6b and 6c in the manner of a bandpass filter, before it impinges on the workpiece 2.

The configuration 1 according to the invention furthermore includes an optical detector 14, which includes according to the embodiment of FIG. 1 a first CCD-line camera 14a and a second CCD-line camera 14b that are disposed, with respect to the movement direction of the workpiece 2, preferably in the same plane as the light sources 6a, 6b and 6c and in each case between two of the light sources, as is indicated in FIG. 1. This alternate spatial configuration of light sources 6a, 6b, 6c and detectors 14a, 14b along a half-arc or arc around the workpiece 2 results in a particularly compact structure and a reduction in disturbing light reflexes which are caused, in particular, by light which is irradiated directly by a light source 6 into the detectors/cameras 14.

As can furthermore be seen in the illustrations of FIG. 1 and FIG. 2, one second optical interference filter 16a, 16b is located upstream of each respective CCD-line camera 14a, 14b. This interference filter, in a wavelength-selective fashion, filters the light emitted by the color pigments in the region of the crack 4 in the manner of a bandpass filter, before it impinges on a respective CCD line 18.1, 18.2 to 18.n of the relevant CCD-line camera 14a, 14b.

In the preferred embodiment of the invention, the wavelength range of the light which is used to excite the color pigments to fluorescence and phosphorescence is preferably 300 nm to 480 nm, and the light of the high-power LEDs 8 exciting the color pigments has a preferably bell-shaped spectrum in a wavelength range between 460 nm and 490 nm, with an intensity maximum of about 470 nm. In this case, the first optical interference filter 12a, 12b, 12c preferably has a transmission range between 380 nm and 480 nm.

In other words, the transmission range of the first optical interference filter 12a, 12b, 12c is within the range of the longwave end of the excitation spectrum of the color pigments, wherein the upper limit of transmission range and excitation spectrum is substantially the same. At the same time, according to the invention, the high-power LEDs 8 irradiate shortwave, in particular blue, light with a very narrow-band wavelength range covering approximately half of the upper limit wavelength (480 nm) of the transmission range of the first interference filter and the excitation spectrum, wherein the intensity maximum (470 nm) of the irradiated light 10a, 10b, 10c lies near the previously mentioned limit wavelength (480 nm) but still below it.

As is furthermore shown in FIG. 1, the two CCD-line cameras 14a and 14b are connected to an electronic evaluation device 20, which preferably reads the signals of the CCD lines 18a, 18b with a speed which is substantially proportional to the speed V of the workpiece 2. The evaluation unit 20, which includes a microprocessor and memory in a known manner, ascertains the presence of a crack 4 in the workpiece 2 from respective signal values of light-sensitive cells 22.1 to 22.n of the CCD lines 18 of the cameras 14a, 14b on the basis of known optical image processing methods.

According to the illustration of FIG. 2, preferably a plurality, for example 64, of CCD lines 18 are disposed on a known CCD chip in each CCD-line camera 14a, 14b, wherein neighboring light-sensitive cells 22.1, 22.2 ... 22.n are disposed along an axis 24 which extends substantially parallel to the movement direction V of the workpiece 2.

In order to increase the detection rate of cracks 4, even with continuous illumination of the workpiece 2 with light of low intensity to the required degree, the signal values, corresponding to the quantity of light which comes in each case, of two neighboring light-sensitive cells 22.1, 22.2 . . . 22.n are added to one another after the reading of the cells by the electronic evaluation unit 20. As a result thereof, a strip-type region 26, shown in FIG. 2, is imaged progressively one after the other on each of the CCD lines 18.1, 18.2 . . . 18.n with a reading speed of the neighboring CCD lines 18.1, 18.2 . . . 18.n. The reading speed is proportional to the speed V of the workpiece 2.

In other words, due to adding up the signal values of the corresponding light-sensitive cells 22.1, 22.2 . . . 22.n and with a speed which is proportional to the workpiece speed V, a static image of the workpiece 2 which moves past is produced on the CCD lines 18. As a result thereof, the option of integrating up the quantity of the fluorescent light detected by the light-sensitive cells in order to increase the resolution of the configuration 1 according to the invention becomes available.

Figure 3:
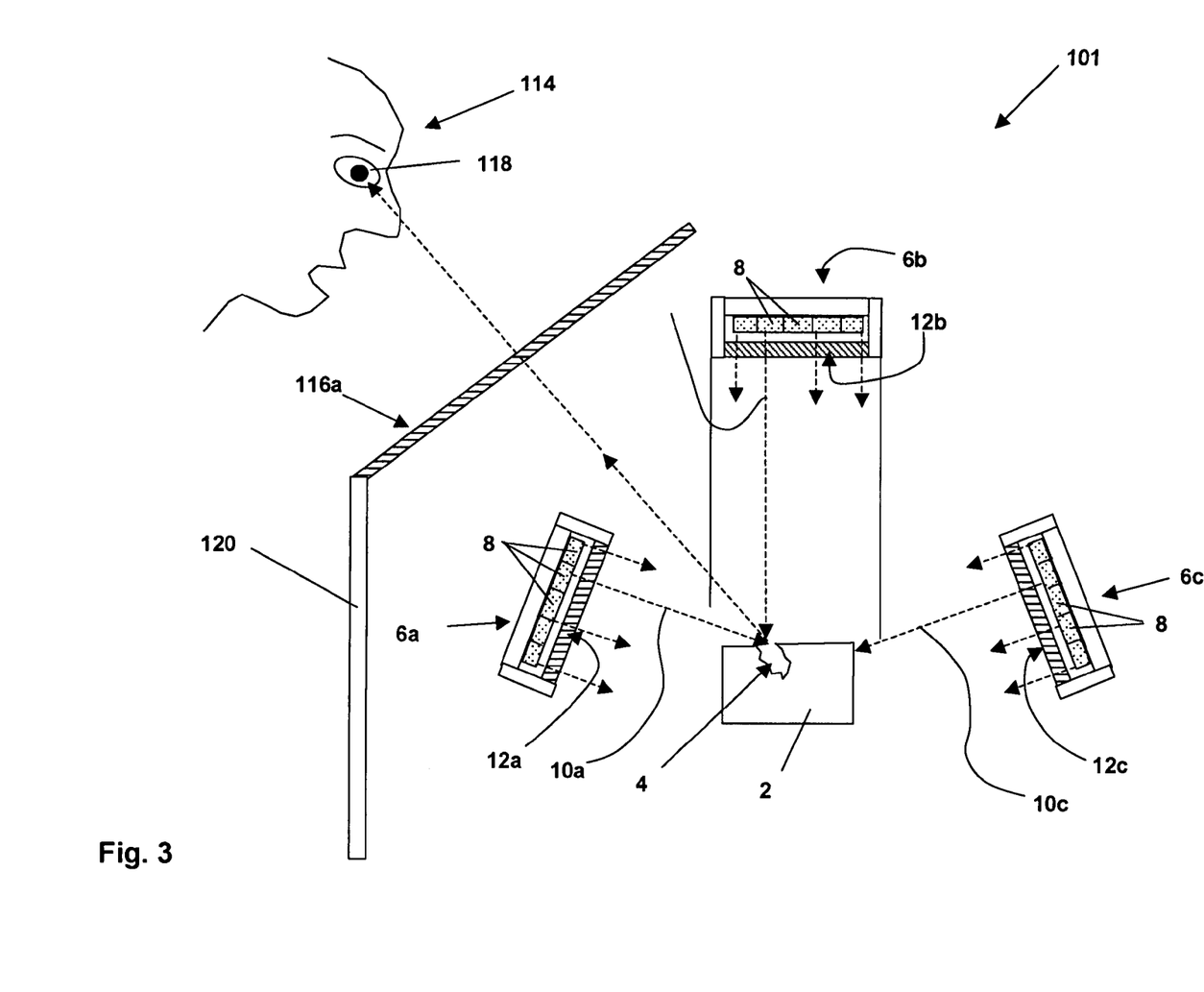
FIG. 3 is a partly perspective, top-plan view of a configuration according to the invention for visually detecting material defects, with a second optical filter in the form of a protective pane and with three light sources overall which are disposed over an angle area of about 160° around a workpiece that moves out of the plane of the drawing and into the latter, for example.

Furthermore, FIG. 3 shows a configuration 101 according to the invention for visually detecting material defects in a workpiece 2, which defects occur, in particular, in the form of cracks 4 that are illustrated in a clearly larger scale in the drawings for illustrative reasons.

The workpiece or workpieces 2 in this case are transported through a non-illustrated transport device, such as a gripper or a conveyor belt, preferably with a constant speed or else are positioned manually on a suitable base.

The workpiece 2 was, before the visual inspection, exposed to a solution in a known manner, for example immersed therein or sprayed with it, with the solution including fluorescing or phosphorescing color pigments which can be excited by shortwave light, for example blue light or UV light, and emitting the irradiated light again as longer-wave fluorescent or phosphorescent light.

The color particles in this case are preferably deposited in cracks 4 of the workpieces 2 and become visible as crack worms when irradiated by using shortwave light in a known manner.

In the configuration 101 according to the invention which is shown in FIG. 3, the shortwave light is preferably produced by three light sources 6a, 6b and 6c, each of each includes a large number of LEDs 8 that are disposed in a planar fashion in one plane, preferably in the manner of a matrix, and emit their light in the form of light beams 10a, 10b and 10c continuously in the direction of the workpiece 2.

One respective first optical filter in the form of an interference filter 12a, 12b and 12c or of an optically active film is disposed between each of the light sources 6a, 6b and 6c and the workpiece 2 in a manner according to the invention. The optical filter selects, in a wavelength-specific manner, the light 10a, 10b and 10c emitted by the light sources 6a, 6b and 6c in the manner of a bandpass filter, before it impinges on the workpiece 2.

As is shown in the illustration of FIG. 3, one second optical filter in the form of a viewing pane 116a made of suitable optical filter material is disposed between the workpiece 2 and an eye 118 of an observer 114 carrying out the visual inspection of the workpiece. The viewing pane is integrated in a diagrammatically-illustrated protective device in the form of a protective viewing wall 120, which allows the observer to see through between the two light sources 6a and 6b to the workpiece 2. The eye 118 of the observer 114 and the light sources 6a, 6b, 6c in this case are preferably located substantially in one plane. The illustrated spatial configuration of the light sources 6a, 6b, 6c along a half-arc or arc around the workpiece 2 results, in combination with the viewing pane 116a disposed between the light sources, in a particularly compact structure of the configuration and a reduction in disturbing light reflexes which are caused, in particular, by light that is irradiated directly by a light source 6 into the eye 118 of the observer 114.

In the preferred embodiment of the invention, the wavelength range of the light which is used to excite the color pigments to fluorescence and phosphorescence is preferably 300 nm to 480 nm, and the light of the high-power LEDs 8 exciting the color pigments has a preferably bell-shaped spectrum in a wavelength range between 460 nm and 490 nm, with an intensity maximum of about 470 nm. In this case, the first optical filter, preferably in the form of an interference filter, 12a, 12b, 12c preferably has a transmission range of between 380 nm and 480 nm.

In other words, the transmission range of the first optical filter 12a, 12b, 12c is within the range of the longwave end of the excitation spectrum of the color pigments, wherein the upper limit of transmission range and excitation spectrum is substantially the same. At the same time, according to the invention, the high-power LEDs 8 irradiate shortwave, in particular blue, light with a very narrow-band wavelength range covering approximately half of the upper limit wavelength (480 nm) of the transmission range of the first optical filter and the excitation spectrum, wherein the intensity maximum (470 nm) of the irradiated light 10a, 10b, 10c lies near the previously-mentioned limit wavelength (480 nm), but still below it.

Figure 4:
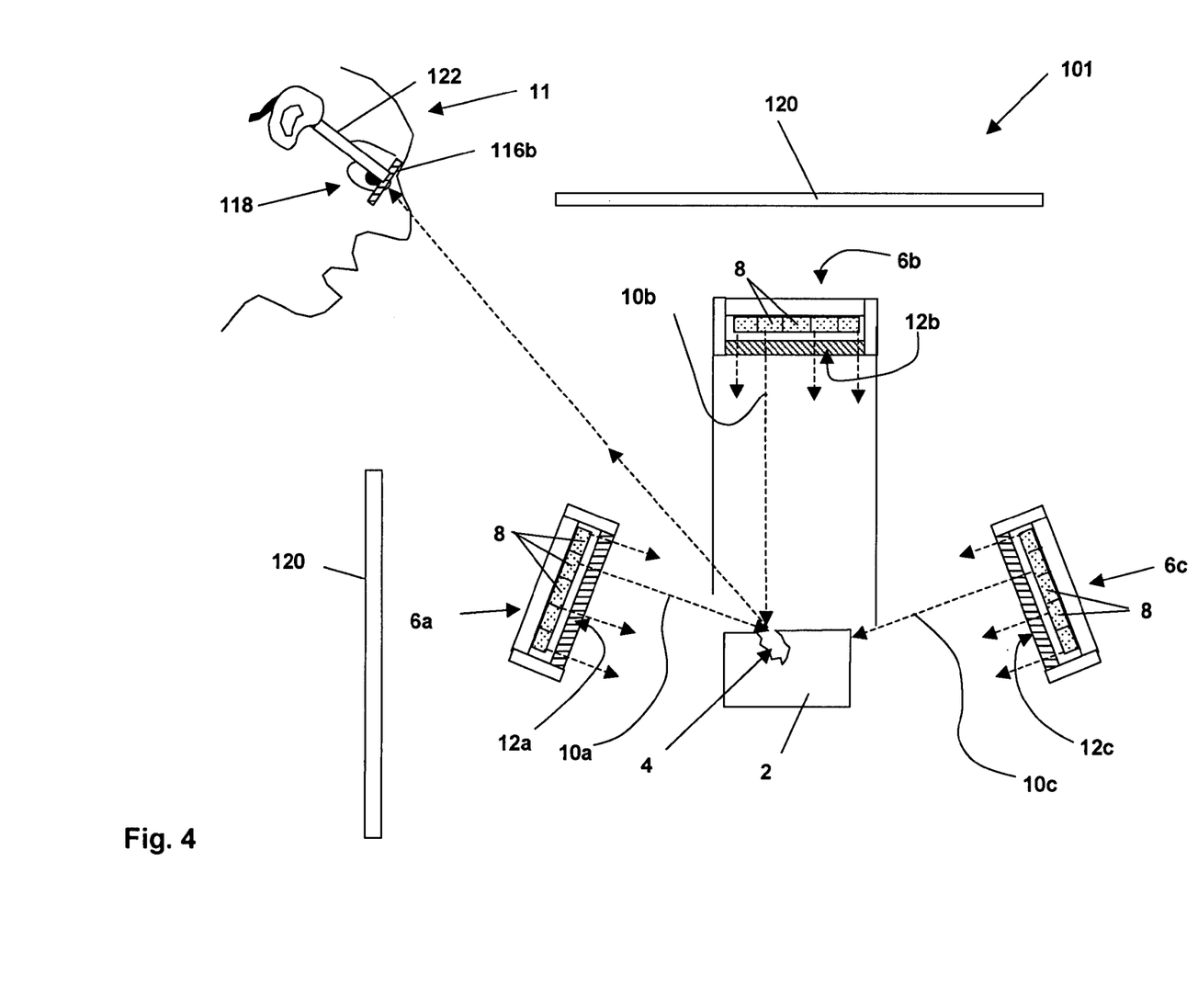
FIG. 4 is a top-plan view of another embodiment of the configuration shown in FIG. 3, in which a second optical filter is held incorporated in protective goggles in the form of a spectacle or eyeglass lens, with an observer wearing the protective goggles for the visual inspection of the workpiece.

According to the illustration of FIG. 4, there is also the option of the observer 114 observing the workpiece 2 through spectacles or eyeglasses 122, which include the second optical filter as a spectacle or eyeglass lens 116b and in which preferably both spectacle or eyeglass lenses 116b are made of the optical filter material, and a side protection which prevents lateral infiltration of light is provided laterally on the spectacle or eyeglass temples. The light may, for example, be daylight or scattered light from one of the light sources 6a, 6b or 6c. The side protection is not shown in FIG. 4 for illustrative reasons.

The invention claimed is:

1. A method for detecting material defects in a workpiece, the method comprising the following steps:
   exposing the workpiece to a test agent containing color pigments to be excited by shortwave light;
   subsequently irradiating the workpiece with shortwave light from a light source having a plurality of LEDs disposed in a matrix, wherein the plurality of LEDs emit bluish light;
   assigning to the light source a first optical interference filter selecting the light emitted by the light source as a bandpass filter, before the light impinges on the workpiece;
   detecting light emitted by the workpiece with a detector; and
   evaluating signals of the detector with an electronic evaluation device for determining the material defects or detecting the light emitted by the workpiece with an eye of a human observer.

2. The method according to claim 1, which further comprises exciting the color pigments with light in a wavelength range between 300 nm and 480 nm, producing light with the light source in a wavelength range between 460 nm and 490 nm, and providing the first optical interference filter with a transmission range between 380 nm and 480 nm.

3. The method according to claim 1, which further comprises assigning to the detector a second optical interference filter selecting the light emitted by the workpiece as a bandpass filter, before the light impinges on the detector.

4. The method according to claim 3, which further comprises emitting light with the color pigments in a wavelength range between 500 nm and 600 nm, and providing the second optical interference filter with a transmission range between 500 nm and 580 nm for the light emitted by the workpiece.

5. The method according to claim 3, which further comprises providing a transmission of at least one of the first optical interference filter or the second optical interference filter in a transmission region above 90%.

6. The method according to claim 3, which further comprises providing a transmission of at least one of the first optical interference filter or the second optical interference filter in a transmission region above 98%.

7. The method according to claim 1, which further comprises moving the workpiece relative to the detector at a speed, providing the detector with a CCD-line camera having at least one CCD line, and reading light-sensitive cells of the at least one CCD line with a speed proportional to the speed of the workpiece.

8. The method according to claim 7, which further comprises carrying out the step of moving the workpiece relative to the detector with a constant speed.

9. The method according to claim 7, which further comprises providing the CCD-line camera, when viewed in a movement direction of the workpiece, with at least first and second adjoining CCD lines having corresponding light-sensitive cells disposed next to each other on an axis, and adding together signal values read from mutually corresponding light-sensitive cells of the first and second CCD lines.

10. The method according to claim 1, which further comprises assigning to the eye of the observer a second optical filter selecting the light emitted by the workpiece as a bandpass filter, before the light impinges on the eye.

11. The method according to claim 10, which further comprises emitting light with the color pigments in a wavelength range between 500 nm and 600 nm, assigning to the detector a second optical interference filter selecting the light emitted by the workpiece as a bandpass filter, before the light impinges on the detector, and providing the second optical filter as an interference filter with a transmission range between 500 nm and 580 nm for the light emitted by the workpiece.

12. The method according to claim 10, which further comprises emitting light with the color pigments in a wavelength range between 500 nm and 600 nm, assigning to the detector a second optical interference filter selecting the light emitted by the workpiece as a bandpass filter, before the light impinges on the detector, and providing the second optical filter as a plastic film with a substantially bell-shaped transmission range between 460 nm and 620 nm for the light emitted by the workpiece and a transmission maximum in a range between 500 nm and 550 nm for the light emitted by the workpiece.

13. The method according to claim 12, which further comprises providing the second optical filter with the transmission maximum in a range between 510 and 530 nm for the light emitted by the workpiece.

14. The method according to claim 1, which further comprises emitting light with the LEDs disposed in the matrix in a wavelength range between 460 nm and 490 nm.

15. The method according to claim 1, which further comprises operating the light source continuously.

16. A configuration for detecting material defects in a workpiece exposed to a test agent containing color pigments to be excited by light, the configuration comprising:

a light source irradiating the workpiece with light, said light source having a plurality of LEDs disposed in a matrix, wherein said plurality of LEDs emit bluish light;

a first optical interference filter associated with said light source for selecting light emitted by said light source as a bandpass filter, before the light impinges on the workpiece;

a detector detecting light emitted by the workpiece; and an electronic evaluation device evaluating signals of said detector for determining the material defects.

17. The configuration according to claim 16, which further comprises a second optical interference filter associated with said detector for selecting the light emitted by the workpiece as a bandpass filter, before the light impinges on said detector.

18. The configuration according to claim 17, wherein the color pigments emit light in a wavelength range between 500 nm and 600 nm, and said second optical interference filter has a transmission range between 500 nm and 580 nm for the light emitted by the workpiece.

19. The configuration according to claim 16, wherein the workpiece is moved relative to said detector at a speed, said detector includes a CCD-line camera with at least one CCD line, and said at least one CCD line is read with a speed proportional to the speed of the workpiece.

20. The configuration according to claim 19, wherein the speed of the workpiece relative to said detector is constant.

21. The configuration according to claim 19, wherein said CCD-line camera, when viewed in a movement direction of the workpiece, includes at least first and second adjoining CCD lines with corresponding light-sensitive cells disposed next to each other on an axis, and signal values read from mutually corresponding light-sensitive cells of said first and second CCD lines are added together to determine the material defect.

22. The configuration according to claim 16, wherein said plurality of LEDs disposed in said matrix emit light in a wavelength range between 460 nm and 490 nm, and said first optical interference filter is one of a plurality of first optical interference filters each assigned to a respective one of said plurality of LEDs.

23. A configuration for detecting material defects in a workpiece exposed to a test agent containing color pigments to be excited by light, the configuration comprising:

a light source irradiating the workpiece with shortwave light exciting the color pigments, said light source having a plurality of LEDs disposed in a matrix, wherein said plurality of LEDs emit bluish light;

a first optical interference filter associated with said light source for selecting light emitted by the light source as a bandpass filter, before the light impinges on the workpiece;

the workpiece emitting light to be detected by an eye of a human observer; and a second optical filter to be associated with the eye of the observer for selecting the light emitted by the workpiece as a further bandpass filter, before the light impinges on the eye of the observer.

24. The configuration according to claim 23, wherein said light source, the workpiece and said second optical filter are disposed spatially in relation to each other to cause light emitted exclusively by the workpiece to directly fall through said second optical filter onto the eye of the observer.

25. The configuration according to claim 23, which further comprises a protection device to be disposed between the eye of the observer and the workpiece, said protection device preventing light scattered laterally past said second optical filter in the direction of the eye of the observer from falling directly onto the eye of the observer.

26. The configuration according to claim 23, which further comprises eyeglasses through which the observer is to observe the workpiece, said eyeglasses including said second optical filter in the form of an eyeglass lens or a viewing pane to be disposed between the workpiece and the observer and including said second optical filter.

27. The configuration according to claim 23, wherein the color pigments emit light in a wavelength range between 500 nm and 600 nm, and said second optical filter is an interference filter with a transmission range between 500 nm and 580 nm for the light emitted by the workpiece.

28. The configuration according to claim 23, wherein the color pigments emit light in a wavelength range between 500 nm and 600 nm, said second optical filter is a plastic film with a substantially bell-shaped transmission range between 460 nm and 620 nm for the light emitted by the workpiece, and the light emitted by the workpiece has a transmission maximum in a range between 500 nm and 550 nm.

29. The configuration according to claim 28, wherein the transmission maximum of the light emitted by the workpiece is in a range between 510 and 530 nm.

30. The configuration according to claim 23, wherein said plurality of LEDs disposed in said matrix emit light in a wavelength range between 460 nm and 490 nm, and said first optical interference filter is one of a plurality of first optical interference filters each assigned to a respective one of said plurality of LEDs.

* * * * *